United States Patent [19]

D'Ambra

[11] Patent Number: 5,663,412

[45] Date of Patent: Sep. 2, 1997

[54] AROMATIC KETONES

[75] Inventor: Thomas E. D'Ambra, Wynantskill, N.Y.

[73] Assignee: Albany Molecular Research, Inc., Albany, N.Y.

[21] Appl. No.: 700,556

[22] Filed: Aug. 8, 1996

Related U.S. Application Data

[60] Continuation of Ser. No. 455,991, May 31, 1995, Pat. No. 5,581,011, which is a division of Ser. No. 382,649, Feb. 2, 1995, abandoned, which is a continuation of Ser. No. 83,102, Jun. 24, 1993.

[51] Int. Cl.$^6$ .............. C07C 69/76; C07C 59/84; C07C 59/88; C07C 59/90
[52] U.S. Cl. .............. 560/51; 560/52; 562/459; 562/463
[58] Field of Search .............. 560/51, 53; 562/459, 562/463

[56] References Cited

U.S. PATENT DOCUMENTS

| | | | |
|---|---|---|---|
| 3,687,956 | 8/1972 | Zivkovic | 546/240 |
| 3,806,526 | 4/1974 | Carr et al. | 546/240 |
| 3,829,433 | 8/1974 | Carr et al. | 546/240 |
| 3,839,431 | 10/1974 | Sheehan et al. | 546/240 |
| 3,862,173 | 1/1975 | Carr et al. | 546/240 |
| 3,878,217 | 4/1975 | Carr et al. | 546/240 |
| 3,898,271 | 8/1975 | Sheehan et al. | 546/240 |
| 3,922,276 | 11/1975 | Duncan et al. | 546/226 |
| 3,931,197 | 1/1976 | Carr et al. | 546/237 |
| 3,941,795 | 3/1976 | Carr et al. | 546/240 |
| 3,946,022 | 3/1976 | Carr et al. | 546/240 |
| 3,956,296 | 5/1976 | Duncan et al. | 544/130 |
| 3,965,257 | 6/1976 | Carr et al. | 514/235.5 |
| 4,028,404 | 6/1977 | Bays et al. | 546/240 |
| 4,254,129 | 3/1981 | Carr et al. | 424/267 |
| 4,254,130 | 3/1981 | Carr et al. | 424/267 |
| 4,285,957 | 8/1981 | Carr et al. | 424/267 |
| 4,285,958 | 8/1981 | Carr et al. | 424/267 |
| 4,407,823 | 10/1983 | Kirsch et al. | 546/240 |
| 4,550,116 | 10/1985 | Soto et al. | 424/267 |
| 4,742,175 | 5/1988 | Fawcett et al. | 546/241 |

FOREIGN PATENT DOCUMENTS

| | | |
|---|---|---|
| 84305268.9 | 3/1985 | European Pat. Off. . |
| WO 93/21156 | 10/1993 | WIPO . |

OTHER PUBLICATIONS

K. Y. Chan, et al., "Direct enantiomeric separation of terfenadine and its major acid metabolite by high-performance liquid chromatography, and the lack of stereoselective terfenadine enantiomer biotransformation in man," *Journal of Chromatography*, 271:291–97 (1991).

F. J. McCarty, et al., "Central Depressants, Phosphoramidates Derived from α,α-Disubstituted 4-Piperidinemethanols," *Department of Organic Research, Scientific Laboratories*, (1961).

Chemical Abstract, vol. 94, 1981, pp. 644, 94:156758e.
Chemical Abstracts, vol. 110, 1989, pp. 762, 110:173097e.
Woosley, R.L., et al., "Mechanism of the Cardiotoxic Actions of Terfenadine," *JAMA* 269 (12):1532–36 (Mar. 1993).

(List continued on next page.)

*Primary Examiner*—Alan L. Rotman
*Assistant Examiner*—Raymond Covington
*Attorney, Agent, or Firm*—Nixon, Hargrave, Devans & Doyle

[57] ABSTRACT

The present invention relates to substantially pure piperidine derivative compounds of the formulae:

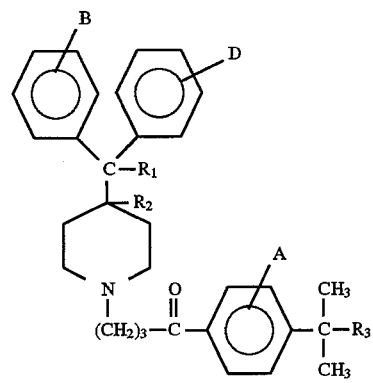

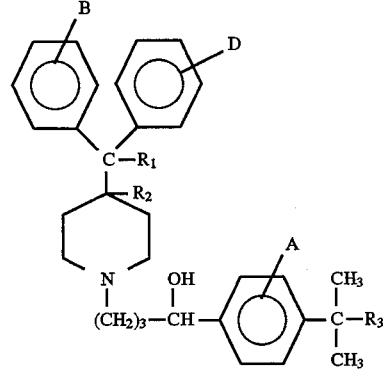

wherein

R$_1$ is hydrogen or hydroxy;

R$_2$ is hydrogen;

or R$_1$ and R$_2$ taken together form a second bond between the carbon atoms bearing R$_1$ and R$_2$;

R$_3$ is —COOH or —COOR$_4$;

R$_4$ has 1 to 6 carbon atoms;

A, B, and D are the substituents of their respective rings each of which may be different or the same and are hydrogen, halogens, alkyl, hydroxy, alkoxy, or other substituents.

A process of preparing such piperidine derivative compounds in substantially pure form is also disclosed.

19 Claims, No Drawings

OTHER PUBLICATIONS

Honig, P.K., et al. "Terfenadine–ketoconazole Interaction. Pharmacokinetic and Electrocardiographic Consequences," *JAMA*, 269 (12):1513–18 (Mar. 1993).

Kuhlman, J.J., Jr., "Measurement of Azacyclonol in Urine and Serum of Humans Following Terfenadine (Seldane) Administration Using Gas Chromatography–mass Spectrometry," *J Chromatogr* 578 (2):207–13 (Jul 1992).

Honig, P.K., et al., "Changes in the Pharmacokinetics and Electrocardiographic Pharmacodynamics of Terfenadine with Concomitant Administration of Erythromycin," *Clin Pharmacol Ther* 52(3): 231–8 (Sep. 1992).

Chen, T.M., et al., "Determination of the Metabolites of Terfenadine in Human Urine by Thermospray Liquid Chromatography–Mass Spectrometry," *J. Pharm. Biomed. Anal.* 9(10–12):929–33, (1991).

Zamani, K., et al., "Enantiomeric Analysis of Terfenadine in Rat Plasma by HPLC," *Chirality*, 3(6):467–70 (1991).

Eller, M.G., et al., "Absence of Food Effects on the Pharmacokinetics of Terfenadine," *Biopharm. Drug Dispos.* 13(3):171–7 (Apr. 1992).

Chan, K.Y., "Direct Enantiomeric Separation of Terfenadine and its Major Acid Metabolite by High–Performance Liquid Chromatography, and the Lack of Stereoselective Terfenadine Enantiomer Biotransformationi n Man," *J. Chromatogr.* 571(1–2) 291–7 (1991).

Eller, M.G., et al., "Pharmacokinetics of Terfenadine in Healthy Elderly Subjects," *J. Clin. Pharmacol.* 32(3):267–71 (Mar. 1992).

Coutant, J.E., et al. "Determination of Terfenadine and Terfenadine Acid Metabolite in Plasma using Solid–Phase Extraction and High–Performance Liquid Chromatography with Fluorescence Detection," *J. Chromatogr.* 570(1):139–48 (1991).

Luo, H., et al. "N(+)–glucuronidation of Aliphatic Tertiary Mines, A General Phenomenon in the Metabolism of H1–antihistamines in Humans," *Xenobiotca.*, 21(10):1281–8 Oct. 1991).

Estelle, F., et al., "Pharmacokinetic Optimisation of Histamine H1–Receptor Antagonist Therapy," *Clin. Pharmacokinet.*, 21(5):372–93 (Nov. 1991).

Shall, L. et al., "Dose–Response Relationship Between Objective Measures of Histamine–Induced Weals and Dose of Terfenadine," *Acta. Derm. Venerol.* 71(3):199–204 (1991).

Campoli–Richards, D.M., et al., "Cetirizine. A Review of its Pharmacological Properties and Clinical Potential in Allergic Rhinitis, Pollen–Induced Asthma, and Chronic Urticaria," *Drugs* 40(5)762–81 (Nov. 1990).

Snowman, A.M., et al., "Cetirizine: Actions on Neurotransmitter Receptors," *J. Allergy Clin. Immunol.* 86(6–2)1025–8 (Dec. 1990).

Berman, B.D., "Perennial Allergic Rhinitis: Clinical Efficacy of a New Antihistamine," *J. Allergy Clin. Immunol.* 86 (68–2)1004–(Dec. 1990).

Monahan, B.P., et al., "Torsades de Pointes Occurring in Association with Terfenadine Use," *JAMA*, 264(21) 2788–90 (Dec. 1990).

Simons, K.J., et al., "Pharmacokinetics and Pharmacodynamics of Terfenadine and Chlorpheniramine In the Elderly," *J. Allergy Clin. Ummunol.* 85(3)540–7 (Mar. 1990).

Sweeney, G.D., et al., "Anti–Allergy and Anti–Asthma Drugs. Disposition in Infancy and Childhood," *Clin. Pharmacokinet*, 17 Suppl (1):156–68 (1989).

Coniglio, A.A., "Effect of Acute and Chronic Terfenadine on Free and Total Serum Phenytoin Concentrations in Epileptic Patients," *Epilepsia* 30(5):611–6 (Sep–Oct 1989).

Mann, K.V., et al., "Nonsedating Histamine H1–Receptor Antagonists," *Clin. Pharm.* 8(5):331–44 (May 1898).

Barenhotz, H.A., "Loratadine: A Non Sedating Antihistamine with Once–Daily Dosing," *DICP* 23(6)44550 (Jun. 1989).

Brion, N., et al., "Lack of Effect of Terfenadine on Theophylline Pharmacokinetics and Metabolism in Normal Subjects," *Br. J. Clin. Pharmacol.*, 27(3)391–5 (Mar. 1989).

Kaliner, M.A., "Non–sedating Antihistamines," *Allergy Proc.* 9(6):649–63 (Nov–Dec 1988).

Maurer, H., et al., "Identification and Differentiation of Alkylamine Antihistamines and Their Metabolites I Urine by Computerized Gas Chromatography–Mass Spectrometry," *J.Chromatogr* 430(1):31–31 (Augl. 1988).

Simons, F.E., et al., "Lack of Subsensitivity to Terfenadine During Long–Term Terfenadine Treatment," *J. Allergy Clin Immunol* 82(6):1068–75 (Dec 1988).

Shall, L., et al., "Assessment of the Duration of Action of Terfenadine on Histamine Induced Weals," *Br. J. Dermatol* 119(4):525–31 (Oct. 1988).

Akagi, M., "Antiallergic Effects of Terfenadine on Immediate Type Hypersensitivity Reactions," *Immunopharmacol Immunotoxicol* 9(2–3):257–79 (1987).

Snyder, S.H., et al., "Receptor Effects of Cetirizine," *Ann Allergy* 59(6–2):4–8 (Dec. 1987).

Simons, F.E., "The Pharmacokinetics and Pharmacodynamics of Terfenadine in Children," *J. Allergy Clin Immunol.* (6):884–90 (1987).

Carter, C.A., et al., "Terfenadine, A Nonsedating Antihistamine," *Drug Intell Clin Pharm* 19(11):812–7 (Nov. 1985).

Paton, D.M., et al., "Clinical Pharmacokinetics of H1–Receptor Antagonists" (He Antihistamines) *Clin Pharmacokinet*, 10(6):477–97 (Nov–Dec 1985).

Woodward, J.K., "Terfenadine, the First Non–Sedating Antihistamine," *Arzneimittelforschung* 32(9a):1154–6 (1982).

Cook, C.E., et al., "Radioimmunoassay for Terfenadine in Human Plasma," *J. Pharm Sci* 69(12):1419–23 (Dec 1980).

Sepracor Inc. Accounces Second Quarter 1993 Financial Results, *Business Wire, Inc.* (Jul. 1993).

Marion Merrell Dow Restructures, *The Financial Times Limited* (Jul. 1993).

Marion Merrell Invests in Sepracor, *Chemical Week Associates* (Jun. 1993).

Sepracor, Inc. Accounces Agreement with Marion, *Business Wire, Inc.* (Jun. 1993).

Sepracor Licenses Rights to Marion Merrell, *Reuters, Limited* (Jun. 1993).

Drug Makers Contend with Inevitable Change, *Chemical Week Associates* (Mar. 1993).

Drug Pipelines Point to a Mixed Future, *Chemical Week Associates* (Mar. 1993).

Not Associated with Cardiac Effects of Leading Prescription, Non–sedative Antihistamines; JAMA Study First to Demonstrate Potential Theraupeutic Benefits of Active Metabolite of Terfenadine, *Business Wire, Inc.* (Mar. 1993).

R.T. Morrison, et al., Organic Chemistry, pp. 661–662 (3rd ed., 1974).

AROMATIC KETONES

This is a continuation of U.S. application Ser. No. 08/455,991, filed May 31, 1995, now U.S. Pat. No. 5,581,011, which is a divisional of U.S. application Ser. No. 08/382,649, filed Feb. 2, 1995, now abandoned, which is a continuation of Ser. No. 08/083,102, filed on Jun. 24, 1993.

FIELD OF THE INVENTION

The present invention relates to piperidine derivatives and a process for their production.

BACKGROUND OF THE INVENTION

Terfenadine, 1-(p-tert-butylphenyl)-4-[4'-(α-hydroxydiphenylmethyl)-1'-piperidinyl]-butanol is a non-sedating anti-histamine. It is reported to be a specific $H_2$-receptor antagonist that is also devoid of any anticholingeric, anti-serotoninergic, and anti-adrenergic effects both in vitro and in vivo. See D. McTavish, K. L. Goa, M. Perrill, *Drugs*, 1990, 39, 552; C. R. Kingsolving, N. L. Monroe, A. A. Carr, *Pharmacologist*, 1973, 15, 221; J. K. Woodward, N. L. Munro, *Arzneim-Forsch*, 1982, 32, 1154; K. V. Mann, K. J. Tietze, *Clin. Pharm.* 1989, 6, 331. A great deal of effort has been made investigating structure-activity relationships of terfenadine analogs, and this is reflected in the large number of U.S. patents disclosing this compound and related structures as follows:

U.S. Pat. No. 3,687,956 to Zivkovic
U.S. Pat. No. 3,806,526 to Carr, et. al.
U.S. Pat. No. 3,829,433 to Carr, et. al.
U.S. Pat. No. 3,862,173 to Carr, et. al.
U.S. Pat. No. 3,878,217 to Carr, et. al.
U.S. Pat. No. 3,922,276 to Duncan, et. al.
U.S. Pat. No. 3,931,197 to Carr, et. al.
U.S. Pat. No. 3,941,795 to Carr, et. al.
U.S. Pat. No. 3,946,022 to Carr, et. al
U.S. Pat. No. 3,956,296 to Duncan, et. al.
U.S. Pat. No. 3,965,257 to Carr, et. al
U.S. Pat. No. 4,742,175 to Fawcett, et. al.

Terfenadine has been linked to potentially fatal abnormal heart rhythms in some patients with liver disease or who also take the antifungal drug ketoconazole or the antibiotic erythromycin. In animal and human metabolic studies, terfenadine was shown to undergo high first-pass effect, which results in readily measurable plasma concentrations of the major metabolite 4-[4-[4-(hydroxydiphenylmethyl)-1-piperidinyl]-1-hydroxybutyl]-α,α-dimethylphenylacetic acid, also known as terfenadine carboxylic acid metabolite. The terfenadine carboxylic acid metabolite also possesses anti-histaminic activity in animal models and may lack the cardiac side effects seen with terfenadine.

Piperidine derivatives related to the terfenadine carboxylic acid metabolite are disclosed in the following U.S. patents:

U.S. Pat. No. 4,254,129 to Carr, et. al.
U.S. Pat. No. 4,254,130 to Carr, et. al.
U.S. Pat. No. 4,285,957 to Carr, et. al.
U.S. Pat. No. 4,285,958 to Carr, et. al.

In the patents, 4-[4-[4-(hydroxydiphenylmethyl)-1-piperidinyl]-1-hydroxybutyl]-α,α-dimethylbenzeneacetic acid and related compounds are prepared by alkylation of a substituted piperidine derivative of the formula:

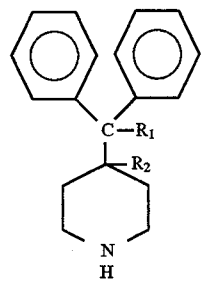

with an ω-haloalkyl substituted phenyl ketone of the formula:

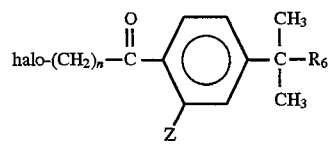

wherein the substituents halo, $R_1$, $R_2$, n, z, and $R_6$ are described in column 6 of U.S. Pat. No. 4,254,130.

It is further described that the ω-haloalkyl substituted phenyl ketone wherein Z is hydrogen are prepared by reacting an appropriate straight or branched lower alkyl $C_{1-6}$ ester of α-α-dimethylphenylacetic acid with the compound of the following formula:

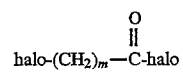

under the general conditions of a Friedel-Crafts acylation, wherein halo and m are described in column 11 of U.S. Pat. No. 4,254,129. The reaction is carried out in carbon disulfide as the preferred solvent.

Applicant has discovered that the preparation of ethyl 4-(4-chloro-1-oxobutyl)-α,α-dimethylphenylacetate by reaction of 4-chlorobutyryl chloride, aluminum chloride, and ethyl α,α-dimethylphenylacetate in carbon disulfide, as described in Example 1 of U.S. Pat. Nos. 4,254,130 and 4,285,958 provides an inseparable mixture of monosubstituted aromatic regioisomers of the formula:

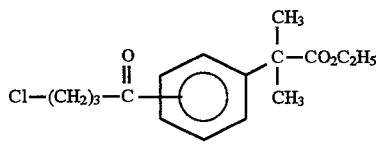

wherein the chlorobutyryl substituent is attached at either of the three aromatic carbons which are meta or para to the dimethylacetate substituent. These regioisomers are not separable by standard techniques of thin layer chromatography, or column chromatography, and low field proton nuclear magnetic resonance spectroscopy is inconclusive in identifying the product of this reaction as a mixture. When the mixture of monosubstituted aromatic regioisomers of the preceding formula is reacted with a piperidine of the formula:

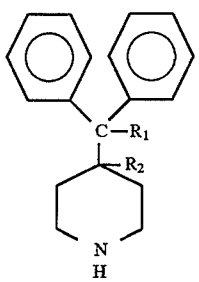

a second mixture of aromatic regioisomers is obtained of the formula:

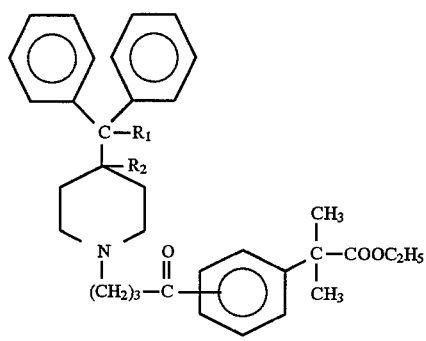

wherein the monosubstituted meta, para mixture of regioisomers is obtained.

It is known in the art that a monoalkyl substituent on a benzene ring is ortho, para directing in electrophilic aromatic substitution reactions such as a Friedel-Crafts reaction. Thus, it would be expected that the Friedel-Crafts reaction of α-chlorobutyryl chloride with ethyl α,α-dimethylphenylacetate would yield predominantly the para substituted product of the formula:

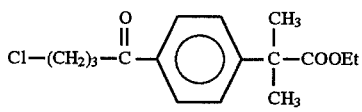

because of the electron donating, para-directing character of the dimethylalkyl substituent combined with the steric hindrance associated with reaction of the ortho positions. In practice, the inductive electronic withdrawing effect of the carboxylic ester of ethyl α,α-dimethylphenylacetate counteracts the expected alkyl electron donating effect, resulting in no significant directing effect for the aromatic substitution reaction. For the described reaction, a statistical mixture of meta to para regioisomers results, with the two meta positions predominating.

The above second mixture of regioisomers can be converted to a third mixture of regioisomers of formula:

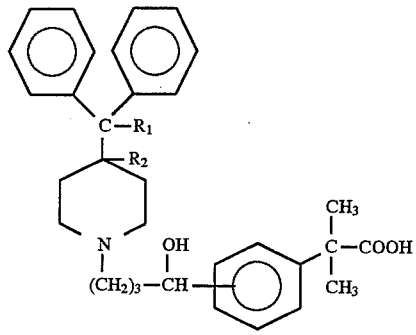

Although the second mixture of regioisomers and the third mixture of regioisomers can be analyzed by HPLC experiments, a practical separation to obtain gram quantities of substantially pure regioisomers has not been achieved. Each mixture (including the first), would be expected to contain 33% of the para isomer and 67% of the meta isomer. Since these components are inseparable, it has not been possible to obtain either of the regioisomers in each mixture in substantially pure form.

SUMMARY OF THE INVENTION

The present invention relates to substantially pure piperidine derivative compounds of the formulae:

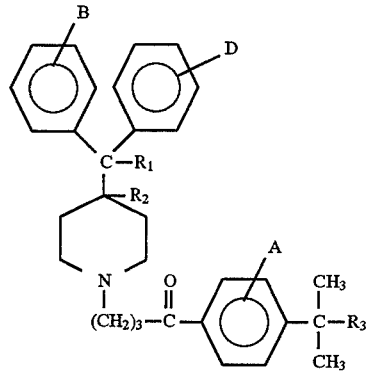

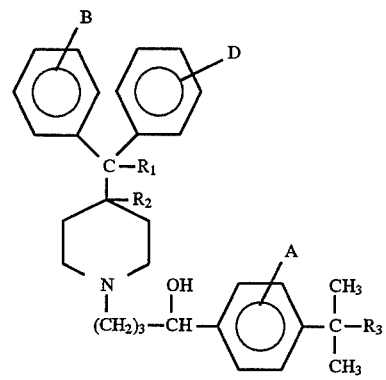

wherein $R_1$ is hydrogen or hydroxy;

$R_2$ is hydrogen;

or $R_1$ and $R_2$ taken together form a second bond between the carbon atoms bearing $R_1$ and $R_2$;

$R_3$ is —COOH or —COOR$_4$;

$R_4$ is an alkyl with 1 to 6 carbon atoms;

A, B, and D are the substituents of their rings, each of which may be different or the same, and are selected from the group consisting of hydrogen, halogens, alkyl, hydroxy, alkoxy, or other substituents or a salt thereof. These compounds are useful in pharmaceutical compositions, particularly is antihistamines, anti-allergy agents, and bronchodilators.

The piperidine derivative compound is prepared by a process which is initiated by providing a substantially pure regioisomer of the following formula:

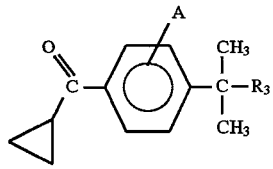

The substantially pure regioisomer is converted to the piperidine derivative having a keto group with a piperidine compound of the formula:

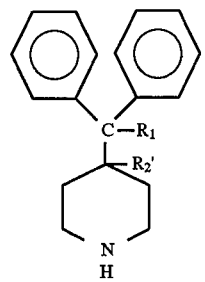

A number of synthetic pathways for preparing the substantially pure regioisomer and for reacting it with the piperidine compound having a keto group are disclosed. The piperidine derivative having a keto group can be converted to the above piperidine derivative having a hydroxyl group by reduction.

Although a wide variety of piperidine derivatives can be produced by the process of the present invention, it is particularly useful in forming a hydroxylated piperidine derivative of the formula:

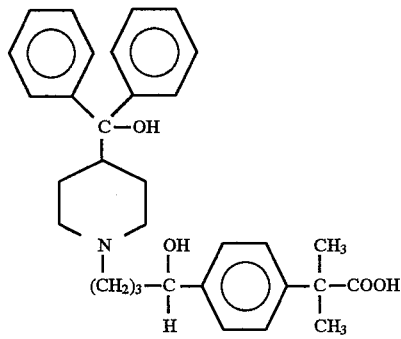

Alternatively, the process of the present invention can be used to produce a piperidine derivative with a keto group of the following formula:

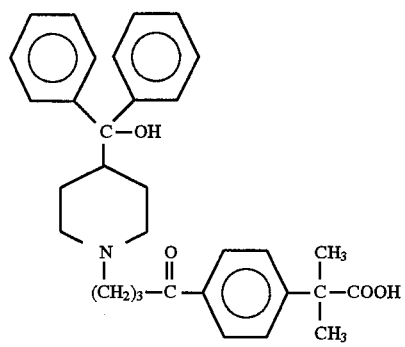

DETAILED DESCRIPTION OF THE INVENTION

The present invention relates to substantially pure piperidine derivative compounds of the formulae:

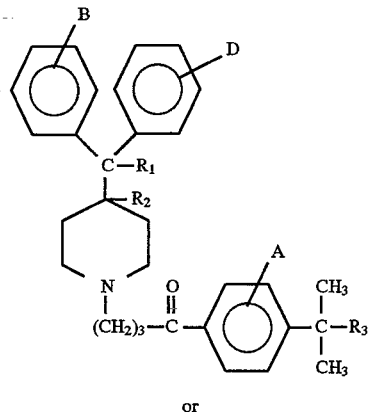

or

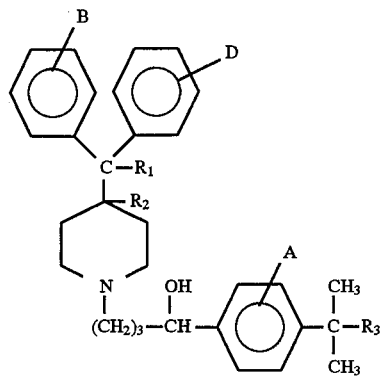

wherein $R_1$ is hydrogen or hydroxy;

$R_2$ is hydrogen;

or $R_1$ and $R_2$ taken together form a second bond between the carbon atoms bearing $R_1$ and $R_2$;

$R_3$ is —COOH or —COOR$_4$;

$R_4$ is an alkyl with 1 to 6 carbon atoms;

A, B, and D are the substituents of their rings, each of which may be different or the same, and are selected from the group consisting of hydrogen, halogens, alkyl, hydroxy, alkoxy, or other substituents or a salt thereof.

These substantially pure piperidine derivative compounds may be in the form of 4-diphenylmethylpiperidine derivatives represented by the following formulae:

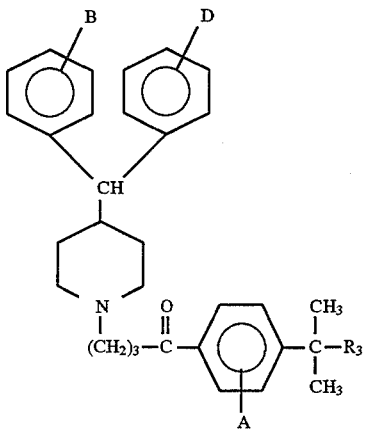

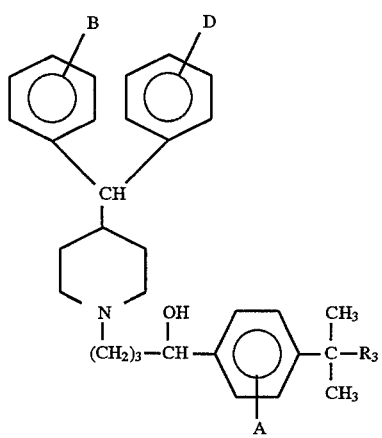

where A, B, D, R₃ are defined above. The substantially pure piperidine derivative compounds include 4-(hydroxydiphenylmethyl)piperidine derivatives according to the following formulae:

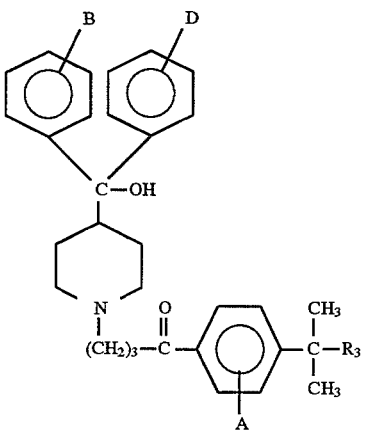

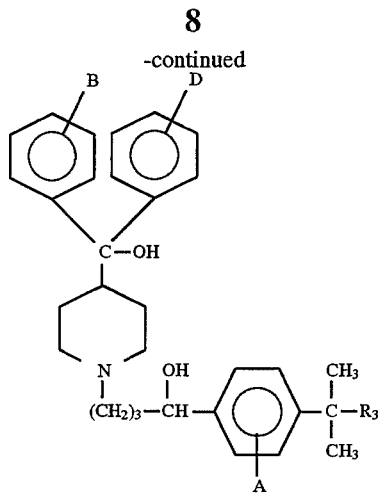

where A, B, D, R₃ are defined above. Another useful class of piperidine derivative compounds are 4-diphenylmethylenepiperidine derivatives in accordance with the following formulae:

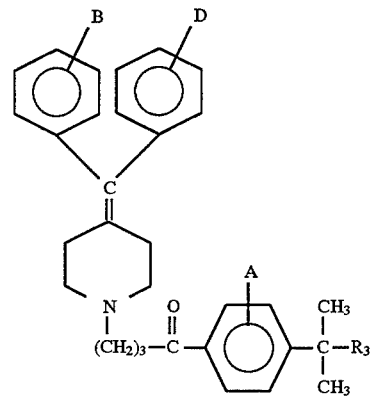

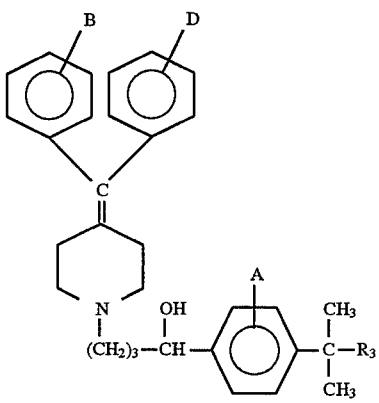

where A, B, D, R₃ are defined above. Examples of $R_4$ are straight or branched alkyl groups, including methyl, ethyl, n-propyl, isopropyl, n-butyl, sec-butyl, tert-butyl, n-pentyl, neopentyl, and n-hexyl groups.

Illustrative examples of compounds of the present invention are as follows:

4-[4-[4-(hydroxydiphenylmethyl)-1-piperidinyl]-1-hydroxybutyl]-α,α-dimethylbenzeneacetic acid;

4-[4-[4-(diphenylmethyl)-1-piperidinyl]-1-hydroxybutyl]-α,α-dimethylbenzeneacetic acid;

4-[4-[4-(diphenylmethylene)-1-piperidinyl]d-hydroxybutyl]-α,α-dimethylbenzeneacetic acid;

4-[4-[4-(hydroxydiphenylmethyl)-1-piperidinyl]-1-hydroxybutyl]-α,α,-dimethyl-3-hydroxybenzeneacetic acid;

5-[4-[4-(hydroxydiphenylmethyl)-1-piperidinyl]-1-hydroxybutyl]-α,α-dimethyl-2-hydroxybenzeneacetic acid;

4-[4-[4-(diphenylmethylene)-1-piperidinyl]-1-hydroxybutyl]-α,α-dimethyl-3-hydroxybenzeneacetic acid;

5-[4-[4-(diphenylmethylene)-1-piperidinyl]-1-hydroxybutyl]-α,α-dimethylbenzeneacetic acid;

ethyl 4-[4-[4-(hydroxydiphenylmethyl)-1-piperidinyl]-1-hydroxybutyl]-α,α-dimethylbenzeneacetic;

n-pentyl 4-[4-[4-(diphenylmethyl)-1-piperidinyl]-1-hydroxybutyl]-α,α-dimethylbenzeneacetate;

ethyl 4-[4-[4-(diphenylmethylene)-1-piperidinyl]-1-hydroxybutyl]-α,α-dimethylbenzeneacetate;

methyl 4-[4-[4-(hydroxydiphenylmethyl)-1-piperidmyl]-1-hydroxybutyl]-α,α-dimethylbenzeneacetate;

ethyl 4-[4-[4-(hydroxydiphenylmethyl)-1-piperidinyl]-1-hydroxybutyl]-α,α-dimethyl-(3-hydroxybenzene)acetate;

n-propyl 4-[4-[4-(hydroxydiphenylmethyl)-1-piperidinyl]-1-hydroxybutyl]-α,α-dimethyl-(2-hydroxybenzene)acetate;

n-hexyl 4-[4-[4-(diphenylmethylene)-1-piperidinyl]-1-hydroxybutyl]-α,α-dimethyl-(3-hydroxybenzene) acetate;

ethyl 5-[4-[4-(diphenylmethylene)-1-piperidinyl]-1-hydroxybutyl]-α,α-dimethylbenzeneacetate;

α,α-diphenyl-1-(4-(4-tert-butyl-2-hydroxy)phenyl)-4-hydroxybutyl-4-piperidinemethanol;

α,α-diphenyl-1-(4-(4-tert-butyl-3-hydroxy)phenyl)-4-hydroxybutyl-4-piperidinemethanol;

α,α-diphenyl-1-(3-(4-tert-butyl-2-hydroxy)phenyl)-3-hydroxypropyl-4-piperidinemethanol;

α,α-diphenyl-1-(5-(4-tert-butyl-2-acetyloxy)phenyl)-5-hydroxypentyl-4-piperidinemethanol;

α,α-diphenyl-1-(4-(4-hydroxy-tert-butyl-2-hydroxy)-phenyl)-4-hydroxybutyl-4-piperidinemethanol;

α,α-diphenyl-1-(4-(4-hydroxy-tert-butyl-3-hydroxy)-phenyl)-4-hydroxybutyl-4-piperidinemethanol;

α,α-diphenyl-1-(3-(4-hydroxy-tert-butyl-2-hydroxy)-phenyl)-3-hydroxybutyl-4-piperidinemethanol;

α,α-diphenyl-1-(4-(4-hydroxy-tert-butyl)phenyl)-4-hydroxybutyl-4-piperidinemethanol;

1-(4-tert-butyl-2-hydroxyphenyl)-4-4-diphenylmethylene)-1-(piperidinyl)butanol;

1-(4-tert-butyl-3-hydroxyphenyl)-4-(4-diphenylmethylene)-1-(piperidinyl)butanol;

1-(4-tert-butyl-3-hydroxyphenyl)-2-(4-diphenylmethylene)-1-(piperidinyl)butanol;

1-(4-tert-butyl-2-butyryloxyphenyl)-6-(4-(diphenylmethyl)-1-piperidinyl)hexanol;

1-(4-hydroxy-tert-butyl-2-hydroxyphenyl)-4-(4-(diphenylmethylene)-1-(piperidinyl)butanol;

1-(4-hydroxy-tert-butyl-3-hydroxyphenyl)-4-(4-(diphenylmethylene)-1-(piperidinyl)butanol;

(4-hydroxy-tert-butylphenyl)-4-(4-(diphenylmethylene)-1-(piperidinyl)butanol;

Particularly preferred are compounds of the formulae:

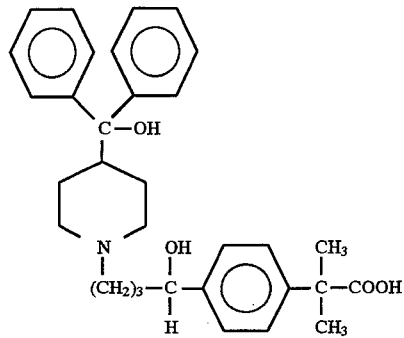

and

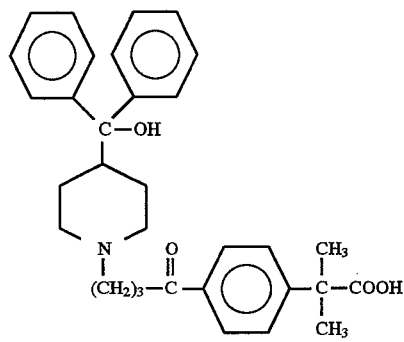

Optionally, both diphenyl groups from the piperidine compound may be alkyl (e.g., methyl) substituted at the position para to the methylene.

This invention also includes pharmaceutically acceptable salts in the form of inorganic or organic acid or base addition salts of the above compounds. Suitable inorganic acids are, for example, hydrochloric, hydrobromic, sulfuric, and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, anthranillic, cinnamic, salicyclic, 4-aminosalicyclic, 2-phenoxybenzoic, 2-acetoxybenzoic, and mandelic acid. Sulfonic acids, such as, methanesulfonic, ethanesulfonic, and β-hydroxyethanesulfonic acid are also suitable acids. Non-toxic salts of the compounds of the above-identified formulas formed with in organic and organic bases include, for example, those alkali metals, such as, sodium, potassium, and lithium, alkaline earth metals, for example, calcium and magnesium, light metals of group IIIA, for example, aluminum, organic amines, such as, primary, secondary, or tertiary amines, for example, cyclohexylamine, ethylamine, pyridine, methylaminoethanol, and piperazine. These salts are prepared by conventional means, for example, by treating the piperidine derivative compounds of the formula:

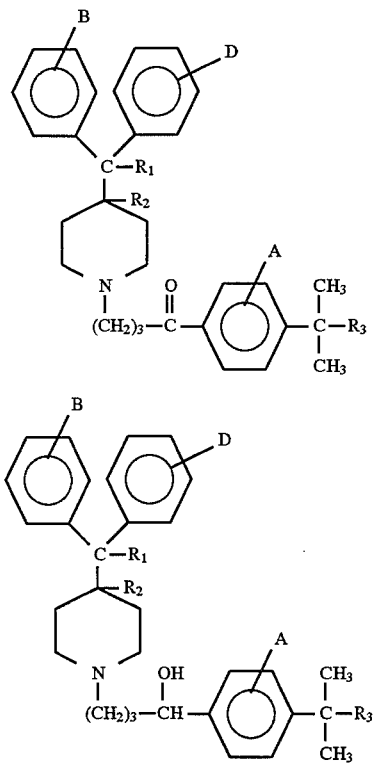

where $R_1$, $R_2$, and $R_3$ are defined above, with an appropriate acid or base.

The piperidine derivative compounds of the present invention can be utilized as the biologically active components in pharmaceutical compositions. The compounds of this invention are useful as antihistamines, antiallergy agents, and bronchodilators. They may be administered alone or with suitable pharmaceutical carriers, and can be in solid or liquid form such as, tablets, capsules, powders, solutions, suspensions or emulsions.

The compounds of this invention can be administered orally, parenterally, for example, subcutaneously,: intravenously, intramuscularly, intraperitoneally, by intranasal instillation or by application to mucous membranes, such as, that of the nose, throat and bronchial tubes. Such application to mucous membranes can be achieved with an aerosol spray containing small particles of a compound of this invention in a spray or, dry powder form.

The quantity of the compound of the present invention administered will vary depending on the patient and the mode of administration and can be any effective amount. The quantity of the compound administered may vary over a wide range to provide in a unit dosage an effective amount of frown about 0.01 to 20 mg/kg of body weight of the patient per day to achieve the desired effect. For example, the desired antihistamine, antiallergy, and bronchodilator effects can be obtained by consumption of a unit dosage form such as a tablet containing 1 to 50 mg of the compound of the present invention taken 1 to 4 times daily.

The solid unit dosage forms can be of the conventional type. This, the solid form can be a capsule, such as an ordinary gelatin type containing the compound of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic add or magnesium stearate.

The compounds of this invention may also be administered in injectable dosages by solution or suspension of the compounds of the present invention in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols the compounds of this invention in solution or suspension may be packaged in a pressurized aerosol container together with suitable propellants, for example, hydrocarbon propellants like propane, butane, or isobutane with conventional adjuvants. The compounds of the present invention also may be administered in a non-pressurized form such as in a nebulizer or atomizer.

The compounds of the present invention can be used to treat warm blooded animals, birds, and mammals. Examples of such beings include humans, cats, dogs, horses, sheep, cows, pigs, lambs, rats, mice, and guinea pigs.

The piperidine derivative compounds of the present invention are prepared by providing a substantially pure regioisomer of the following formula:

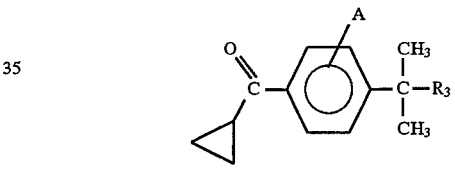

and then converting the substantially pure regioisomer to the piperidine derivative compounds of the invention having a keto group with a piperidine compound of the formula:

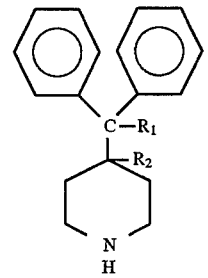

The resulting piperidine derivative compounds with a keto group can be converted by reduction to the above-described piperidine compounds with a hydroxyl group.

There are several techniques of providing these substantially pure regioisomers.

Process One For Producing Substantially Pure Regioisomer

In one embodiment of the present invention, the substantially pure regioisomer is formed by initially acylating a starting compound of the formula:

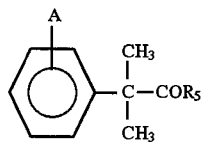

wherein $R_5$ is $-OR_6$, $-N(R_6)_2$, and $-SR_6$, and $R_6$ is an alkyl with 1 to 6 carbons, with a compound of the formula:

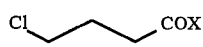

wherein

X is a halogen, under conditions effective to produce a first mixture of regioisomers of the formula:

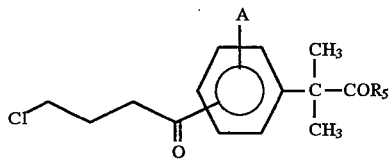

Such conditions include those conventionally utilized in a Friedel-Crafts acylation reaction catalyzed by, for example, $AlCl_3$. The reaction is carried out in a solvent such as, carbon disulfide, tetrachloroethane, or nitrobenzene with carbon disulfide being the preferred solvent. The reaction is carried out for a time period of ½ to 12 hours, preferably 3 to 5 hours, at a temperature of 0° to 25° C.

The first mixture of regioisomers can be hydrolyzed under conditions effective to form a second mixture of regioisomers of the formula:

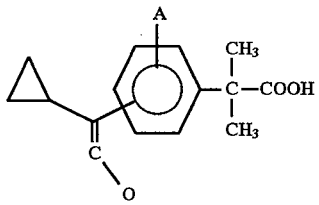

Typically this reaction is carried out by base hydrolysis procedures which are well known in the art. For example, the first mixture of regioisomers can be treated with an inorganic baser such as, sodium hydroxide or potassium hydroxide, in an aqueous lower alcohol solvent. Suitable solvents include aqueous methanol, ethanol, isopropanol, or n-butanol solutions. Hydrolysis is carded out at reflux temperatures of the solvent for ½ to 12 hours.

Following such hydrolyzation, the substantially pure regioisomer of the formula:

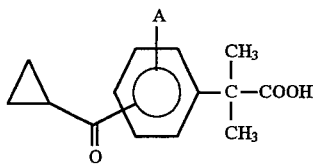

is recovered from the second mixture of regioisomers. Such recovery is carried out by crystallizing the substantially pure regioisomer salt of the formula:

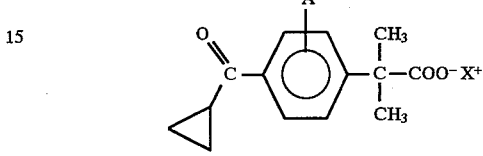

wherein $X^+$ is a Lewis Acid

Such crystallization is carried out by fractional crystallization techniques known in the art. Generally, such procedures involve dissolving the second mixture of regioisomers in a solvent containing a salt at temperatures of 20° C. to the reflux temperature of the solvent. The resulting solution is then slowly cooled to temperatures of −20° to 25° C.

Suitable solvents for fractional crystallization include: alcohol solvents, like methanol, ethanol, isopropyl alcohol, and n-butanol; ketone solvents, such as acetone or methyl ethyl ketone; ester-containing solvents, like ethyl acetate or isopropyl acetate; ethereal solvents such as tetrahydrofuran; acetonitrile; and dimethylformamide. Ethyl acetate is preferred.

Suitable salts for fractional crystallization are those where $X^+$ is an alkali metal salt, like sodium and potassium salts, or, more preferably, ammonium salts of the form $NR_7R_8R_9$, where $R_7$, $R_8$, and $R_9$ is hydrogen or a straight or branched alkyl of 1 to 6 carbon atoms which may be substituted at any position with a phenyl ring or a substituted phenyl ring. The ammonium salt can also be cinchonidine, quinine, quinidine, quinudidine, brucine, thebaine, or cinchonine. Of these salt complexes, cinchonidine is preferred.

The substantially pure regioisomer salt is then isolated by filtration and converted to the substantially pure regioisomer of the formula:

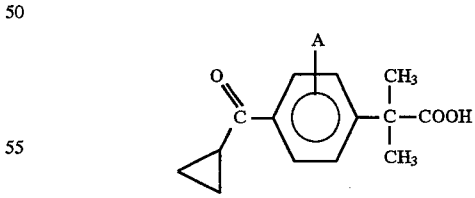

by procedures well known in the art. Typically, such conversion is accomplished by treatment with acid.

Process Two For Producing Substantially Pure Regioisomer

In another embodiment of the process of the present invention, the substantially pure regioisomer is produced by acylating a starting compound of the formula:

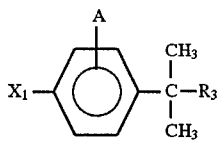

wherein

R₃ is —COOH, —COOalkyl, —CON(alkyl)₂, —COSalkyl where the alkyl moieties have 1 to 6 carbon atoms and are straight or branched with a compound of the formula:

wherein

X₁ is a halogen, trialkyl tin, trialkyl borate, triflate, or organometallic reagents of lithium or magnesium derived from bromine or iodine, with any alkyl groups having 1 to 4 carbon atoms and being straight or branched under conditions effective to produce the substantially pure regioisomer of the formula:

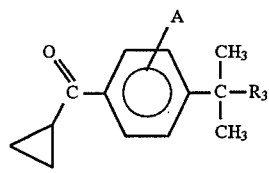

This acylation reaction is carried out in a suitable solvent in the presence of an appropriate catalyst for about 1 to 120 hours and at temperatures of about 0° C. to the reflux temperature of the solvent. Suitable solvents for acylation include: hydrocarbon solvents, such as benzene, toluene, xylene, or cyclohexane; halogenated hydrocarbons, such as chlorobenzene, dichloroethane, methylene chloride, chloroform, or carbon tetrachloride; carbon disulfide; dimethylformamide; ethereal solvents, like tetrahydrofuran and diethylether; or dioxane.

A variety of catalysts may be utilized when A is hydrogen. Suitable catalysts include palladium catalysts, like palladium chloride, palladium acetate, tetrakis(triphenylphosphine)palladium(O), dichlorobis(triphenylphosphine palladium(II), or benzylchlorobis(triphenylphosphine)palladium(H); or nickel-phosphine catalysts. Acylation may also be carried out in the presence of added lithium chloride or triphenylphosphine. The latter acylation reaction is known in the art as organometallic cross coupling reactions and are conducted by the general procedures of D. Milstein, et al., *J. Org. Chem.*, 1979, 44, 1613; J. W. Labadie, et al., *J. Org. Chem.*, 1983, 48, 4634; C. Sahiberg, et al., *Tetrahedron Letters*, 1983, 24, 5137; D. Milstein, et al., *J. Am. Chem. Soc.*, 1978, 100, 3636; and K. Tamao, et al., *Tetrahedron*, 1982, 38, 3347.

Process Three For Producing Substantially Pure Regioisomer

In another embodiment of the process of the present invention, the substantially pure regioisomer is produced by acylating a starting compound of the formula:

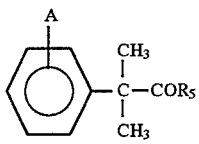

wherein

R₅ is —OR₆, —N(R₆)₂, and —SR₆, and

R₆ is an alkyl with 1 to 6 carbon atoms with a compound of the formula:

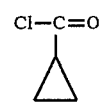

under conditions effective to produce a first mixture of regioisomers of the formula:

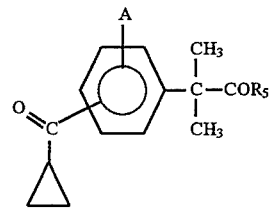

Typically, such acylation is carried out by a Friedel-Crafts reaction, as described above in Process One for Producing Substantially Pure Regioisomers.

The substantially pure regioisomer salt is recovered by fractional crystallization, isolation, and converting, as described above with reference to Process One for Producing Substantially Pure Regioisomers.

Once the substantially pure regioisomer of the present invention produced by one of the above (or some other) process, there are a number of procedures for using that compound to produce the piperidine derivatives of the present invention.

Process One Of Converting The Substantially Pure Regioisomer to The Substantially Pure Piperidine Derivative Having A Keto Group According to one aspect of the present invention, the substantially pure regioisomer can be halogenated under conditions effective to form a first intermediate compound of the formula:

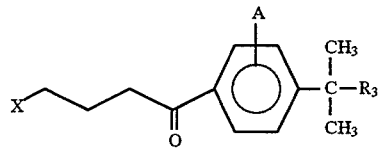

wherein X is a halogen.

Suitable halogens include chlorine, bromine, and iodine. Suitable conditions for carrying out such halogenating include reacting the substantially pure regioisomer with a halogen nucleophile and a Lewis Acid. The ring opening reaction is carried out in a suitable solvent, optionally in the presence of a catalytic amount of base for about 0.5 to 24 hours and a temperature of about −40 degrees C to the reflux temperature of the solvent. Suitable halogen nucleophiles include sodium iodide, sodium bromide, potassium iodide, potassium bromide, cesium iodide, cesium bromide, trimethylsilyl iodide, manganese iodide, cerium iodide, magnesium bromide, magnesium iodide, magnesium carbonate, calcium bromide, and calcium iodide. Suitable Lewis Acids include silicon compounds such as trimethylsilyl chloride and trimethylsilyl iodide; aluminum compounds such as aluminum chloride, trimethyl aluminum, diethyl aluminum chloride, ethyl aluminum dichloride, and diethyl aluminum cyanide; magnesium salts; and boron salts. Suitable solvents for the ring opening reaction include hydrocarbon solvents, such as, benzene, toluene, xylene, or cyclohexane; ethereal solvents such as ether, tetrahydrofuran, dioxane or dimethoxyethane; or halogenated hydrocarbons, such as, chlorobenzene, methylene chloride, carbon tetrachloride, chloroform, or dichloroethane.

After such halogenation, the first intermediate compound is reacted with a piperidine compound of the formula:

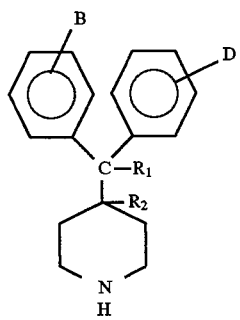

under conditions effective to form the piperidine derivative compound having a keto group of the formula:

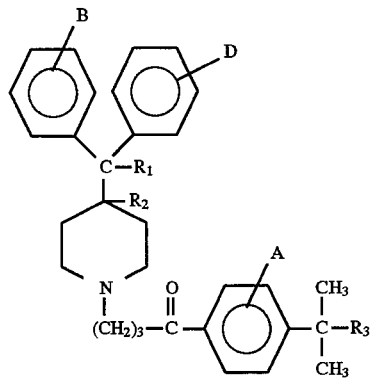

This alkylation reaction is carried out in a suitable solvent preferably in the presence of a base and, optionally, in the presence of a catalytic amount of potassium iodide for about 4 to 120 hours at a temperature of about 70° C. to the reflux temperature of the solvent. Suitable solvents for the alkylation reaction include alcohol solvents, such as, methanol, ethanol, isopropyl alcohol, or n-butanol; ketone solvents, such as, methyl isobutyl ketone; hydrocarbon solvents, such as, benzene, toluene, or xylene; halogenated hydrocarbons, such as, chlorobenzene or methylene chloride; or dimethylformamide. Suitable bases for the alkylation reaction include inorganic bases, for example, sodium bicarbonate, potassium carbonate, or potassium bicarbonate or organic bases, such as a trialkylamine, for example, triethylamine or pyridine, or an excess of the piperidine compound can be used.

When $R_3$ is —COOalkyl, the alkylation reaction is followed by base hydrolysis to convert $R_3$ substituents that are —COOalkyl groups to —COOH groups. Such base hydrolysis involves treatment of the substantially pure piperidine derivative with an inorganic base; such as, sodium hydroxide in an aqueous lower alcohol solvent, such as, aqueous methanol, ethanol, isopropyl alcohol, or n-butanol at reflux temperature for about ½ hour to 12 hours.

Piperidine compounds where each of $R_1$ and $R_2$ is hydrogen or wherein $R_1$ is hydroxy and $R_2$ is hydrogen are commercially available or may be prepared according to procedures well known in the art (e.g. F. J. McCarty, C. H. Tilford, M. G. Van Campen, *J. Am. Chem. Soc.*, 1961, 26, 4084). Piperidine compounds wherein $R_1$ and $R_2$ form a second bond between the carbon atoms bearing $R_1$ and $R_2$ may be prepared by dehydration of the corresponding compound wherein $R_1$ is hydroxy by procedures generally known in the art.

Second Process For Converting Substantially Pure Regioisomer To Substantially Pure Piperidine Derivative Having A Keto Group In another embodiment of the present invention, the substantially pure regioisomer of the formula:

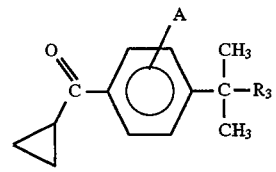

is reacted directly with a piperidine compound of the formula:

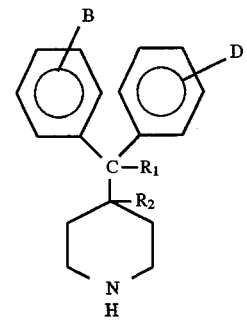

under conditions effective to form the piperidine derivative compound having a keto group of the formula:

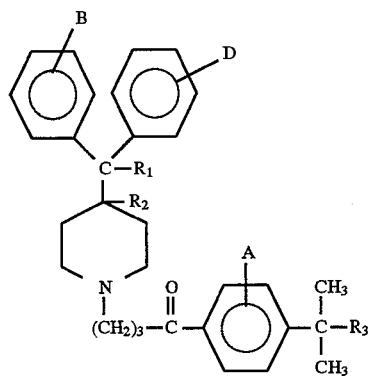

This alkylation reaction is carried out in a suitable solvent preferably in the presence of a base and optionally in the presence of a Lewis Acid such as magnesium, cesium, or calcium salts or trimethylsilyl chloride or in the presence of a catalytic amount of potassium iodide for about 4 to 120 hours at a temperature of about 70°C. to the reflux temperature of the solvent. Suitable solvents for the alkylation reaction include alcohol solvents, such as, methanol, ethanol, isopropyl alcohol, or n-butanol; ketone solvents, such as, methyl isobutyl ketone; hydrocarbon solvents, such as, benzene, toluene, or xylene; and halogenated hydrocarbons, such as, chlorobenzene or methylene chloride; or dimethylformamide. Suitable bases of the alkylation reaction include inorganic bases, for example, sodium bicarbonate, potassium carbonate, or potassium bicarbonate or organic bases, such as, a trialkylamine, for example, triethylamine or pyridine, or an excess of a compound of the piperidine compound may be used.

Processes for Reduction of Keto Group in Substantially Pure Piperidine Derivative As discussed above, the process of the present invention is useful in producing substantially pure piperidine derivatives with either a keto group or a hydroxyl group. Derivatives with keto groups can be converted to similar compounds with hydroxyl groups by reduction reactions. Which are well known in the art.

Reduction can be carried out with sodium borohydride or potassium borohydride in lower alcohol solvents, such as, methanol, ethanol, isopropyl alcohol, or n-butanol.

When lithium aluminum hydride or diborane are used as reducing agents, suitable solvents are ethers, for example, diethyl ether, tetrahydrofuran, or dioxane. These reduction reactions are carried out at temperatures ranging from about 0° C. to the reflux temperature of the solvent, and the reaction time varies from about 0.5 to 8 hours.

Catalytic reduction may also be employed using, for example, Raney nickel, palladium, platinum or rhodium catalysts in lower alcohol solvents, such as, methanol ethanol isopropyl alcohol or n-butanol or acetic acid or their aqueous mixtures, or by the use of aluminum isopropoxide in isopropyl alcohol. Reduction using sodium borohydride is generally preferred over catalytic reduction when forming carboxylic acids or esters. When the starting material is an ester, lithium aluminum hydride is the preferred reducing agent, while diborane is preferred when starting with an acid.

When esters with hydroxyl groups have been formed, base hydrolysis can be used to produce a carboxylic acid. Such procedures are well known and generally involve treatment with an inorganic base, such as, sodium hydroxide or potassium hydroxide, in an aqueous lower alcoholic solvent, such as aqueous methanol ethanol isopropyl alcohol or n-butanol. Base hydrolysis is carried out at about the solvent reflux temperature for about ½ hour to 12 hours.

EXAMPLES

Example 1

Preparation of Ethyl 3- and 4-(4-Chloro-1-oxobutyl)-α,α-dimethylphenylacetate

Aluminum chloride (44 g; 0.33 mol) was added slowly in portions to a solution of freshly distilled 4-chlorobutyryl chloride (17 mL;0.15 mol) in 460 mL of carbon disulfide at −10° C. under a nitrogen atmosphere. The mixture was stirred for 15 minutes, then the cooling bath was removed and the mixture was allowed to warm to ambient temperature. The mixture was stirred then for 15 minutes more, then cooled again to −10° C. and a solution of ethyl α,α-dimethylphenyl acetate (26.6 g; 0.14 mol in 70 mL of carbon disulfide was added dropwise. The mixture was maintained with stirring for 3 hr, then stirred overnight at room temperature.

The reaction mixture was partitioned between $H_2O$ and $CHCl_3$. The combined organic portions were washed with saturated aqueous $NaHCO_3$ solution, dried over $MgSO_4$, filtered and concentrated in vacuo. The residue was dissolved in $CH_2Cl_2$ and filtered through a plug of $SiO_2$, eluting with 10% EtOAc in hexane. Concentration of the product containing fractions afforded 39.4 g of ethyl 3- and 4-(4-chloro4-oxobutyl)-α,α-dimethylphenylacetate as a mixture of aromatic regioisomers.

Example 2

Preparation of 4-(Cylopropyl-oxo-methyl)-α,α-dimethylphenylacetic acid.

To a solution of 39.4 g of ethyl 3- and 4-(4-chloro-1-oxobutyl)-α,α-dimethylphenylacetate obtained in Example 1 dissolved in 800 mL of $CH_3OH$ and 200 mL of $H_2O$ was added 40 g of NaOH. The resulting mixture was refluxed for one hour. The cooled mixture was then concentrated in vacuo to remove the $CH_3OH$. The concentrate was diluted with $H_2O$ and washed with two portions of EtOAc. The aqueous layer was acidified with concentrated HCl and extracted with two portions of EtOAc. The extracts were dried over $MgSO_4$, filtered, and concentrated in vacuo to afford 30.3 g of crude product.

The crude product was dissolved in 600 mL of EtOAc, 38 g of cinchonidine was added, and the mixture was stirred overnight. The resulting solids were filtered and washed with ELOAc and sucked dry under a rubber dam to afford 25 g of a tan solid.

The solids were partitioned between EtOAc and 2NHCl. The aqueous layer was extracted with EtOAc. The combined organics were dried over $MgSO_4$, filtered, and concentrated in Vacuo to afford 10.6 g of an oil (33% from ethyl α,α-dimethyl-phenylacetate).

Example 3

Preparation of 4-(4-Iodo-1-oxobutyl)-α,α-dimethylphenylacetic acid

A solution of 10.5 g of 4-(cyclopropyl-oxo-methyl)-α,α-dimethylphenylacetic acid, prepared in accordance with Example 2, in 250 mL of $CH_2Cl_2$ was cooled in an ice-MeOH bath and 25 g of trimethylsilyliodide was then added rapidly via pipette. The mixture was stirred in the ice bath for one hour, warmed to ambient temperature, and stirred for one hour. A solution of aqueous sodium bisulfite was then added and the mixture was stirred well. The phases were partitioned and the aqueous layer was extracted with $CH_2Cl_2$. The combined organics were washed with saturated aqueous NaCl, dried over $MgSO_4$, filtered, and concentrated in vacuo to afford 12.6 g (77%) of 4-(4-iodo-1-oxobutyl)-α,α-dimethylphenylacetic acid.

Example 4

Preparation of Methyl-4-(4-Iodo4-oxobutyl)-α,α-dimethylphenylacetate

To a solution of 12.6 g of 4-(4-iodo-1-oxobutyl-α,α-dimethylphenylacetic acid, prepared in accordance with Example 3, in 100 mL of $Et_2O$ cooled in an ice bath, was added 40 mL of ethereal CH$_2$N$_2$. The mixture was stirred at 0° C. for few minutes, then let stand for 2 hr. A few drops of AcOH were added to decompose excess CH$_2$N$_2$, then the mixture was filtered and stripped to afford 12.6 g (96%) of methyl 4-(4-iodo-1-oxobutyl)-α,α-dimethylphenylacetate.

Example 5

Preparation of Methyl 4-[4-[4-(Hydroxydiphenylmethyl)-1-piperidinyl]4-oxobutyl] -α,α-dimethylphenylacetate A solution of 12.6 g of methyl 4-(4-iodo-1-oxobutyl)-α, α-dimethylphenylacetate, prepared in accordance with Example 4, in 500 mL of toluene in a one liter three neck flask with mechanical stirring was added 8.8 g of 4-(α,α-diphehyl)piperidinemethanol and 23 g of K$_2$CO$_3$ and the mixture was refluxed for 7 hr. The cooled reaction mixture was then filtered and concentrated in vacuo. The residue was dissolved in Et$_2$O and treated with excess ethereal HCl. The mixture was then concentrated to a solid. The solid was treated with EtOAc and collected by filtration. The product was then partitioned between EtOAc and 2N Na$_2$CO$_3$. The organics were dried over MgSO$_4$, filtered, and concentrated in vacuo to afford 13.5 g (79%) of methyl 4-[4-[4-(hydroxydiphenylmethyl)-1-piperidinyl]-1-oxobutyl]-α,α-dimethylphenylacetate.

Example 6

Preparation of Methyl 4-[4-[4-(Hydroxydiphenylmethyl)-1-piperidinyl]-1-hydroxybutyl]-α,α-dimethylphenylacetate A solution of 13.5 g of methyl 4-[4-[4-(hydroxydiphenylmethyl)-1-piperidinyl]-1-oxobutyl]-α,α-dimethylphenylacetate, prepared in accordance with Example 5, in 250 mL of CH$_3$OH was cooled in an ice CH$_3$OH bath and 1.8 g of NaBH$_4$ was added in portions. After 1 hr, the mixture was concentrated to a solid. The residue was partitioned between EtOAc and saturated aqueous NaHCO$_3$. The aqueous portion was extracted with EtOAc. The combined organics were washed with saturated aqueous NaCl, dried over MgSO$_4$, filtered, and concentrated in vacuo to afford 9.5g (70%) of methyl 4-[4-[4-(hydroxydiphenylmethyl)-1-piperidinyl]-1-hydroxybutyl]-α,α-dimethylphenylacetate as a foam.

Example 7

Preparation of 4-[4-[4-Hydroxydiphenylmethyl)-1-piperidinyl]-1-hydroxy-butyl]-(α,α-dimethylphenylacetic Acid To a solution of 9.5 g of methyl-4-[4-[4-(hydroxydiphenylmethyl)-1-piperidinyl]-1-hydroxybutyl]-α,α-dimethylphenylacetate, prepared in accordance with Example 6, in 300 mL of CH$_3$OH and 150 mL of H$_2$O was added 10 g of NaOH. The mixture was refluxed for 1 hr, then cooled. The CH$_3$OH was removed in vacuo. The concentrate was diluted with H$_2$O and CHCl$_3$ and the pH adjusted to approximately 5.5 to 6.0. The phases were separated and the aqueous phase was extracted with CHCl$_3$. The combined organics were dried over MgSO$_4$, filtered, and stripped to afford 9.0 g of crude product.

The crude product was dissolved in CH$_2$Cl$_2$ and chromatographed on Davish Grade 633 SiO$_2$ eluting with a gradient of CHCl$_3$, to 10% CH$_3$OH in CHCl$_3$, to 25% CH$_3$OH in CHCl$_3$. The product containing fractions were concentrated to afford 5.2 g of white crystals. An analytical sample was prepared by treatment of the product with EtOAc, mp 199°–203° C. Calc. for C$_{32}$H$_{39}$NO$_4$: C, 76.62; H, 7.84; N, 2.79. Found: C, 76.24; H, 7.76; N, 2.75.

Example 8

Preparation of Methyl 4-[4-[4-(Bis(4-methylphenyl) hydroxymethyl)-1-piperidinyl]-1-oxobutyl]-α,α-dimethylphenylacetate To a solution of 6.4 g (0.017 mol) of methyl 4-(4-iodo-1-oxobutyl)-α,α-dimethylphenylacetate, prepared in accordance with Example 4, in 500 mL of toluene in a one liter round bottom flask equipped with a mechanical stirrer was added 5.1 g (0.017 mol of 4-(α,α-bis(4-methylphenyl)-piperidinemethanol, followed by 11.8 g (0.086 mol) of solid potassium carbonate. The solution was heated to reflux for 24 hr. After cooling, the mixture was filtered and the toluene was removed in vacuo. The residue was partitioned between ethyl acetate and 2N sodium bicarbonate solution. The aqueous layer was extracted twice with ethyl acetate, the combined organic layers were dried with sodium sulfate and the ethyl acetate was removed in vacuo to provide 6.8 g (73%) of methyl 4-[4-[4-(bis(4-methylphenyl) hydroxymethyl-1-piperidinyl]-1-oxobutyl]-α,α-dimethylphenylacetate as a viscous, dark colored oil.

Example 9

Preparation of Methyl 4-[4-[4-(Bis(4-Methylphenyl) hydroxymethyl)-1-piperidinyl]-1-hydroxybutyl]-α, α-dimethylphenylacetate To a −10° C. solution of 6.8 g (0.013 mol) of methyl 4-[4-[4-bis (4-methylphenyl)hydroxymethyl)-1-piperidinyl] -1-oxobutyl]-α,α-dimethylphenylacetate, prepared in accordance with Example 8, in 150 mL of methanol in a 500 mL round bottom flask equipped with a mechanical stirrer was slowly added 0.86 g (0.023 mol) of sodium borohydride, and the reaction was stirred for 2 hr. The methanol was removed in vacuo and the residue was partitioned between ethyl acetate and aqueous sodium bicarbonate solution. The aqueous layer was extracted with ethyl acetate, the combined organic layers were dried with sodium sulfate, and the ethyl acetate was removed in vacuo to provide 6.9 g of a dark colored foam. The resultant material was purified by column chromatography (Davisil grade 633 silica gel, packed in methylene chloride, material applied in chloroform, and eluted with a gradient of 2% methanol to methylene chloride to 5% methanol to methylene chloride) to afford 5.3 g (77%) of methyl 4-[4-[4-(bis( 4-methylphenyl)hydroxymethyl)-1-piperidinyl]-1-hydroxybutyl]-α,α-dimethylphenylacetate.

Example 10

Preparation of 4-[4-[4-(Bis(4-methylphenyl) hydroxymethyl)-1-piperidinyl]-1-hydroxybutyl]-α, α-dimethylphenylacetic Acid To 350 mL of methanol in a 1 L round bottom flask equipped with a mechanical stirrer was added 5.3 g (9.8 mmol) of methyl 4-[4-[4-(bis(4-methylphenyl) hydroxymethyl)-1-piperidinyl]-1-hydroxybutyl]-α,α-dimethylphenylacetate, prepared in accordance with Example 9, 5.1 g (0.13 mol) of solid sodium hydroxide, and 100 mL of water. The mixture was heated to reflux for 3 hr. After cooling, the methanol was removed in vacuo, and 6N hydrochloric acid was added dropwise until the solution was no longer basic (pH =7). The solution was extracted three times with ethyl acetate. The organic layers were combined and a white crystalline solid precipitated out of solution. The solid was washed with ether to provide 1.8 g (34%) of 4-[4-[4-(bis(4-methylphenyl) hydroxymethyl)-1-piperidinyl]-1-hydroxybutyl]-α,α-dimethylphenylacetic acid, as the dihydrate, mp 208°–215° C. Analysis. Calcd. for $C_{34}H_{43}NO_4$-2($H_2O$): C, 72.18; H, 8.37; N, 2.47. Found: C, 72.02; H, 8.36; N, 2.41.

Example 11

Preparation of 4-(1-Hydroxy-4-iodobutyl)-α,α-dimethylphenylacetic acid

To a solution of 50 mg of 4-(4-iodo-1-oxobutyl)-α,α-dimethylphenylacetic acid, prepared in accordance with Example 3, in 3 mL of methanol was added 50 mg of $NaBH_4$. The mixture was stirred for 30 minutes, acidified with 2N HCl, and the methanol removed in vacuo. The concentrate was extracted with EtOAc. The organics were dried over $Na_2SO_4$, filtered, and concentrated to afford 40 mg of 4-(1-hydroxy-4-iodobutyl)-α,α-dimethylphenylacetic acid.

Example 12

Preparation of 4-[4-[4-(Hydroxydiphenylmethyl)-1-piperidinyl]-1-oxobutyl]-α,α-dimethylphenylacetic acid A mixture of 800 mg of 4-(4-iodo-1-oxobutyl)-α,α-dimethylphenylacetic acid, prepared in accordance with Example 3, 800 mg of 4-(α,α-diphenyl)piperidinemethanol, and 2.4 g of $K_2CO_3$ in 25 mL of toluene was stirred for 48 hours at room temperature. The mixture was concentrated in vacuo. The residue was treated with EtOAc, filtered, and concentrated to afford 4-[4-[4-(hydroxydiphenylmethyl)-1-piperidinyl]-1-oxobutyl]-α,α-dimethylphenylacetic acid.

Example 13

Preparation of 4-[4-[4-Hydroxydiphenylmethyl)-1-piperidinyl]-1-hydroxybutyl]-α,α-dimethylphenylacetic Acid A mixture of 4-[4-[4-(hydroxydiphenylmethyl)-1-piperidinyl]-1-oxobutyl]-α,α-dimethylphenylacetic acid, prepared in accordance with Example 12, and 300 mg of $NaBH_4$ in 25 mL of $CH_3OH$ was stirred overnight at room temperature. The mixture was then concentrated in vacuo. The residue was partitioned between EtOAc and $H_2O$. The aqueous portion was treated with concentrated HCl until pH 6, then extracted with EtOAc. The organics were concentrated in vacuo. The residue was dissolved in EtOAc, filtered, and concentrated in vacuo to an oil. The oil was dissolved in $CH_3OH$ and concentrated to a solid. The solid was slurried with EtOAc, filtered, and rinsed with EtOAc to afford 4-[4-[4-hydroxydiphenylmethyl)-1-piperidinyl]-1-hydroxybutyl]-α,α-dimethylphenylacetic acid.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A substantially pure regioisomer having the formula:

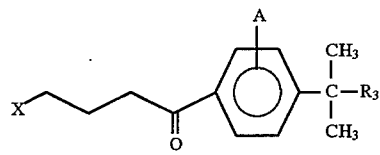

wherein

X is a halogen;

$R_3$ is —COOH or —COOR$_4$;

$R_4$ is an alkyl with 1 to 6 carbon atoms;

A is the substituents of its ring, each of which may be different or the same, and are selected from the group consisting of hydrogen, halogens, alkyl, hydroxy, or alkoxy.

2. A substantially pure regioisomer according to claim 1, wherein each substituent A is a hydrogen.

3. A substantially pure regioisomer according to claim 1, wherein X is chlorine.

4. A substantially pure regioisomer according to claim 1, wherein X is bromine.

5. A substantially pure regioisomer according to claim 1, wherein X is iodine.

6. A substantially pure regioisomer according to claim 1, wherein $R_3$ is —COOH.

7. A substantially pure regioisomer according to claim 1, wherein $R_3$ is —COOR$_4$.

8. A substantially pure regioisomer according to claim 1, wherein X is chlorine and $R_3$ is —COOH.

9. A substantially pure regioisomer according to claim 1, wherein X is bromine and $R_3$ is —COOH.

10. A substantially pure regioisomer according to claim 1, wherein X is iodine and $R_3$ is —COOH.

11. A substantially pure regioisomer according to claim 1, wherein X is chlorine and $R_3$ is —COOR$_4$.

12. A substantially pure regioisomer according to claim 1, wherein X is bromine and $R_3$ is —COOR$_4$.

13. A substantially pure regiozsomer according to claim 1, wherein X is iodine and $R_3$ is —COOR$_4$.

14. A substantially pure regioisomer according to claim 1, wherein each substituent A is a hydrogen and X is chlorine.

15. A substantially pure regioisomer according to claim 1, wherein each substituent A is a hydrogen and X is iodine.

16. A substantially pure regioisomer according to claim 1, wherein each substituent A is a hydrogen and $R_3$ is —COOH.

17. A substantially pure regioisomer according to claim 1, wherein each substituent A is a hydrogen and $R_3$ is —COOR$_4$.

18. A substantially pure regioisomer according to claim 1, wherein each substituent A is a hydrogen, X is chlorine, and $R_3$ is —COOH.

19. A substantially pure regioisomer according to claim 1, wherein each substituent A is a hydrogen, X is chlorine, and $R_3$ is —COOR$_4$.

* * * * *